US009642796B2

(12) United States Patent
Packhaeuser et al.

(10) Patent No.: US 9,642,796 B2
(45) Date of Patent: May 9, 2017

(54) PHARMACEUTICAL DOSAGE FORM FOR ORAL ADMINISTRATION OF A BCL 2 FAMILY INHIBITOR (75) Inventors: Claudia Packhaeuser, Mannheim (DE); Norbert Steiger, Lingenfield (DE); Bernd Liepold, Dossenheim (DE); Drazen Kostelac, Roemerberg (DE); Martin Knobloch, Neuhofen (DE)

(73) Assignee: AbbVie Inc., North Chicago, IL (US)

( * ) Notice: Subject to any disclaimer, the term of this patent is extended or adjusted under 35 U.S.C. 154(b) by 128 days.

(21) Appl. No.: 12/796,000

(22) Filed: Jun. 8, 2010

(65) Prior Publication Data

US 2010/0310648 A1 Dec. 9, 2010

Related U.S. Application Data (60) Provisional application No. 61/185,130, filed on Jun. 8, 2009.

(51) Int. Cl.
*A61K 9/48* (2006.01)
*A61K 9/00* (2006.01)
*A61K 9/14* (2006.01)
*A61K 31/635* (2006.01)

(52) U.S. Cl.
CPC ............ *A61K 9/0053* (2013.01); *A61K 9/146* (2013.01); *A61K 31/635* (2013.01)

(58) Field of Classification Search
CPC ...... A61K 9/10; A61K 31/427; A61K 31/505; A61K 31/513; A61K 31/635; A61K 47/14; A61K 47/22; A61K 9/0053; A61K 9/146; C07D 239/49; C07D 239/69
See application file for complete search history.

(56) References Cited

U.S. PATENT DOCUMENTS

| | | | |
|---|---|---|---|
| 5,536,729 A | 7/1996 | Waranis et al. |
| 5,538,737 A | 7/1996 | Leonard et al. |
| 5,559,121 A | 9/1996 | Harrison et al. |
| 5,635,187 A | 6/1997 | Bathurst et al. |
| 5,645,856 A | 7/1997 | Lacy et al. |
| 5,665,379 A | 9/1997 | Herslöf et al. |
| 5,707,648 A | 1/1998 | Yiv |
| 5,891,469 A | 4/1999 | Amselem |
| 6,004,973 A | 12/1999 | Guitard et al. |
| 6,267,985 B1 | 7/2001 | Chen et al. |
| 6,309,663 B1 | 10/2001 | Patel et al. |
| 6,451,339 B2 | 9/2002 | Patel et al. |
| 6,464,987 B1 | 10/2002 | Fanara et al. |
| 6,964,946 B1 | 11/2005 | Gutierrez-Rocca et al. |
| 7,151,188 B1 | 12/2006 | Simandan et al. |
| 7,390,799 B2 | 6/2008 | Bruncko et al. |
| 7,459,283 B2 | 12/2008 | Wertz et al. |
| 7,842,681 B2 | 11/2010 | Elmore et al. |
| 7,973,161 B2 | 7/2011 | Bruncko et al. |
| 8,168,784 B2 | 5/2012 | Franczyk, II et al. |
| 8,377,952 B2 | 2/2013 | Rosenberg et al. |
| 8,927,009 B2 | 1/2015 | Tong et al. |
| 2002/0055631 A1 | 5/2002 | Augeri et al. |
| 2005/0101628 A1 | 5/2005 | Jiao et al. |
| 2005/0163835 A1 | 7/2005 | Gellert et al. |
| 2005/0208082 A1 | 9/2005 | Papas et al. |
| 2005/0236236 A1 | 10/2005 | Farooq |
| 2006/0177430 A1 | 8/2006 | Bhushan et al. |
| 2006/0183776 A9 | 8/2006 | Pratt |
| 2007/0027135 A1 | 2/2007 | Bruncko et al. |
| 2007/0072860 A1 | 3/2007 | Bruncko et al. |
| 2007/0104780 A1 | 5/2007 | Lipari et al. |
| 2007/0161681 A1 | 7/2007 | Marfat et al. |
| 2007/0243257 A1 | 10/2007 | Bedos et al. |
| 2008/0004286 A1 | 1/2008 | Wang et al. |
| 2008/0085313 A1 | 4/2008 | Given et al. |
| 2008/0182845 A1 | 7/2008 | Bardwell et al. |
| 2009/0149461 A1 | 6/2009 | Krivoshik |
| 2010/0233251 A1 | 9/2010 | Von Andrian et al. |
| 2010/0278905 A1 | 11/2010 | Catron et al. |
| 2010/0278921 A1 | 11/2010 | Fischer et al. |
| 2010/0280031 A1 | 11/2010 | David et al. |
| 2010/0297194 A1 | 11/2010 | Catron et al. |
| 2010/0305122 A1 | 12/2010 | Bruncko et al. |
| 2010/0305125 A1 | 12/2010 | Borchardt et al. |
| 2010/0311751 A1 | 12/2010 | Schmitt et al. |
| 2010/0323020 A1 | 12/2010 | Gokhale et al. |

(Continued)

FOREIGN PATENT DOCUMENTS

CN 1561201 A 1/2005
CN 1706371 A 12/2005

(Continued)

OTHER PUBLICATIONS

Tse et al. 2008. ABT-263: A potent and orally bioavailable bcl-2 family inhibitor. Cancer Res; 68(9): 3421-3428.*
Sharma D.K., et al., "Solubility Enhancement Strategies for Poorly Water-Soluble Drugs in Solid Dispersions: A Review", Asian Journal of Pharmaceutics, 2007,vol. 1 (1), pp. 9-19.
Park C.M., et al. "Discovery of an Orally Bioavailable Small Molecule Inhibitor of Prosurvival B-Cell Lymphoma 2 Proteins," Journal of Medicinal Chemistry, 2008, vol. 51 (21), pp. 6902-6915.
Brandrup J. et al., "Polymer Handbook," 1975, 2, John Wiley & Sons, Inc.

(Continued)

*Primary Examiner* — David Browe (57) ABSTRACT

The invention relates to a pharmaceutical dosage form which comprises a solid dispersion product comprising N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide or a salt, hydrate or solvate thereof, at least one pharmaceutically acceptable polymer, and at least one pharmaceutically acceptable solubilizer. The invention is further directed to processes for preparing the pharmaceutical dosage form and to use of the dosage form for treating proliferative disorders.

22 Claims, 4 Drawing Sheets (56) References Cited

U.S. PATENT DOCUMENTS

| | | | |
|---|---|---|---|
| 2011/0071151 A1 | 3/2011 | Zhang et al. | |
| 2015/0021339 A1 | 1/2015 | Felts et al. | |

FOREIGN PATENT DOCUMENTS

| | | | | |
|---|---|---|---|---|
| CN | 101175738 A | 5/2008 | | |
| CN | 101220008 A | 7/2008 | | |
| CN | 101325944 A | 12/2008 | | |
| CN | 101798292 A | 8/2010 | | |
| CN | 102131792 A | 7/2011 | | |
| EP | 1 880 715 A1 * | 1/2008 | ............... | A61K 9/20 |
| RU | 2008123798 A | 12/2009 | | |
| WO | 9703654 A2 | 2/1997 | | |
| WO | WO0057854 A2 | 10/2000 | | |
| WO | WO0100175 A1 | 1/2001 | | |
| WO | 0224636 A2 | 3/2002 | | |
| WO | 03028705 A1 | 4/2003 | | |
| WO | 2005039551 A2 | 5/2005 | | |
| WO | 2005049593 A2 | 6/2005 | | |
| WO | 2007043057 A2 | 4/2007 | | |
| WO | WO2007040650 A2 | 4/2007 | | |
| WO | 2008009689 A1 | 1/2008 | | |
| WO | 2008123798 A1 | 10/2008 | | |
| WO | 2008124878 A1 | 10/2008 | | |
| WO | 2009073835 A1 | 6/2009 | | |
| WO | WO2009073835 A1 | 6/2009 | | |
| WO | 2009155386 A1 | 12/2009 | | |
| WO | 2010127190 A1 | 11/2010 | | |
| WO | 2010127198 A1 | 11/2010 | | |
| WO | 20100127193 A1 | 11/2010 | | |
| WO | 2010143074 A2 | 12/2010 | | |
| WO | 2011034934 A1 | 3/2011 | | |

OTHER PUBLICATIONS

Bruncko M., et al, "Studies leading to potent, dual inhibitors of Bcl-2 and Bcl-xL" Journal of Medicinal Chemistry, 2007, 50 (4), 641-662.
Fiedler H. B., Encyclopedia of Excipients: For Pharmaceuticals, Cosmetics and Related Areas (Der Pharmazeutische Betrieb), 5th Edition, Editio-Cantor 2002.
Hanahan D., et al., "The Hallmarks of Cancer", Cell, 2000;100: pp. 57-70.
Hovorka S.W., et al., "Oxidative degradation of pharmaceuticals: Theory, mechanisms and inhibition", Journal of Pharmaceutical Sciences, 2001; 90 (3): 253-269.
Sperling L. H., "Introduction to Physical Polymer Science," 1992, 2, John Wiley & Sons, Inc.
Sutton V.R., et al. "Bcl-2 prevents apoptosis induced by perforin and granzyme B, but not that mediated by whole cytotoxic lymphocytes", Journal of Immunology, 1997, 158 (12), pp. 5783-5790.
Tse et al., "Abt-263: A Potent and Orally Bioavailable Bcl-2 Family Inhibitor," Cancer Research , 2008, 68 (9), pp. 3421-3428.
Anonymous: "Phosal™ 53 MCT"[Online] Feb. 2007, XP002601344 Phospholipid GmbH—American Lecithin Retrieved from the Internet: URL:http//www.americanlecithin.com/TDS/TDS_53MCT.PDF.
Berge et al., "Pharmaceutical Salts," Journal of Pharmaceutical Sciences, 66(1):1-19 (Jan. 1977).
Brittain et al., Polymorphism I Pharmaceutical Solids, 1999, Chapter 1, pp. 1-10, and Chapter 5, pp. 183-226.
Brittain et al., "Effects of pharmaceutical processing on drug polymorphs and solvates," Polymorphism in Pharmaceutical Solids, 1999, vol. 95, pp. 331-361.
Byrn et al., "Pharmaceutical Solids: A Strategic Approach to Regulatory Considerations," Pharmaceutical Research, 1995, vol. 12, No. 7, pp. 945-954.
Caira, "Crystalline Polymorphism of Organic Compounds," Topics in Current Chemistry, 1998, 198:163-204.
Chawla et al., "Polymorphism of pharmaceuticals: Challenges and opportunities," Article, Oct. 23, 2003, pp. 3, www.expresspharmaonline.com/20031023/edito2.shtml.

Extended European Search Report issued for EP 2515883 on Jun. 17, 2013, pp. 7.
Gould, "Salt selection for basic drugs," International Journal of Pharmaceutics, Nov. 1986, 33(1-3):201-217.
International Search Report for Application No. PCT/IB2010/001659, mailed on Dec. 13, 2010, pp. 12.
Lessene et al., "BLC-2 family antagonists for cancer therapy," Nature Reviews / Drug Discovery, Dec. 2008, vol. 7, pp. 989-1000, Macmillan Publishers Limited.
Paolini et al., Global mapping of pharmacological space, Jul. 2006, vol. 24, No. 24, pp. 805-815, Nature Biotechnology.
SkypePharma, DissoCubes[online], 2010 [retrived on Nov. 17, 2012]. 1 page, Retrieved from the Internet: <URL:http//www.skyepharma.com/Technology/Oral_Technology_Particle_Engineering_Technologies/DissoCubes/Default. aspx?id=81.
Trotta, Michele et al., "Stability of drug-carrier emulsions containing phosphatidylcholine mixtures," European Journal of Pharmaceutics and Biopharmaceutics, Jun. 11, 2001, vol. 53, pp. 203-208.
Wang et al., "An Efficient Synthesis of ABT-263, A Novel inhibitor of Antiapoptotic Bcl-2 Proteins," Synthesis, Jun. 11, 2008, vol. 15, pp. 2398-2404.
Wendt, Michael D., "Discovery of ABT-263, a Bcl-family protein inhibitor: observations on targeting a large protein-protein interaction," Expert Opinion Drug Discovery, 2008, vol. 3(9), pp. 1123-1143.
Crowley, M. et al.; "Pharmaceutical Applications of Hot-Melt Extrusion: Part 1"; Drug Development and Industrial Pharmacy, vol. 33, 2007, pp. 909-926.
Design and Evaluation of Oral Administration Drugs, 1995, pp. 172-179.
Holzelova, E. et al.; "Autoimmune Lymphoproliferative Syndrome with Somatic Fas Mutations", The New England Journal of Medicine, vol. 351, 2004, pp. 1409-1418.
Kibbe et al., Handbook of Pharmaceutical Excipients, 2000, 3rd Edition, Table of Contents, 4 pages.
Klein, C. et al., "The Tablet Formulation of Lopinavir/Ritonavir Provides Similar Bioavailability to the Soft-Gelatin Capsule Formulation With Less Pharmacokinetic Variability and Diminished Food Effect", Journal of Acquired Immune Deficiency Syndromes, 2007, vol. 44; pp. 401-410.
Moschwitzer, J. et al., "Development of an intravenously injectable chemically stable aqueous omeprazole formulation using nanosuspension technology", European Journal of Pharamaceutics and Biopharmaceutics, vol. 58, 2004, pp. 615-619.
Puck, J. et al., "Immune Disorders Caused by Defects in the Caspase Cascade", Current Allergy and Asthma Reports, vol. 3, 2003, pp. 378-384.
Rengan R., et al., "Actin cytoskeletal function is spared, but apoptosis is increased, in WAS patient hematopoietic cells", Blood, vol. 95 (4) 2000, pp. 1283-1292.
Shimazaki, K. et al., "Evaluation of apoptosis as a prognostic factor in myelodysplastic syndromes"; British Journal of Haematology, vol. 110, 2000, pp. 584-590.
Shoemaker et al., "Activity of the Bcl-2 Family Inhibitor ABT-263 in a Panel of Small Cell Lung Cancer Xenograft Models", Clinical Cancer Research, Jun. 1, 2008, vol. 14, No. 11, pp. 3268-3277.
Sophie et al., "Synthesis of "Trioxaquantel" Derivatives as Potential New Antischistosomal Drugs", European Journal of Organic Chemistry, 2008, pp. 895-913.
AusPAR Circadin, Australian Public Assessment Report for Melatonin, Commercial Eyes Pty Ltd, Dec. 2009, pp. 1-57.
"Biopharmaceutical Classification System and Formulation Development", Technical Brief 2011, Particle Sciences, Drug Development Services, vol. 9, 4 pages.
Buhler, (http://www.innovate-excipients.basf.com/Documents/ENP/Brochure/EN/GEMPMD256_Kollidon_Polyvinylpyrrolidone_excipients_for_the_pharmaceutical_industry.pdf; Mar. 2008), 2 pages.
Dash et al., "Role of Biopharmaceutical Classification System in Drug Development Program", Journal of Current Pharmaceutical Research 2011, vol. 5. No. 1, pp. 28-31.

(56) References Cited

OTHER PUBLICATIONS

Formulations Platform Report 1; Intra-Agency Agreement Between the Eunice Kennedy Shriver National Institute of Child Health and Human Development (NICHD) and the U.S. Food and Drug Administration (FDA) Oral Formulations Platform-Report 1; (http://www.acceessdata.fda.gov/scripts/cder/drugsatfda/index.cfm?fuseaction= Reports.ReportsMenu), 14 pages.

Sachan, et al., "Biopharmaceutical classification system: A strategic tool for oral drug delivery technology", Asian Journal of Pharmaceutics, 2009, vol. 3, Issue 2, pp. 76-81.

Varma (European Journal of Pharmaceutical Sciences 25 (2005), pp. 445-453).

Wu et al., Predicting Drug Disposition via Application of BCS: Transport/Absorption/Elimination Interplay and Development of a Biopharmaceutics Drug Disposition Classification System; Pharmaceutical Research, vol. 22, No. 1, Jan. 2005; pp. 11-23.

Yasir, et al., "Biopharmaceutical Classification System: An Account", International Journal of Pharm Tech Research, Jul.-Sep. 2010, vol. 2, No. 3, pp. 1681-1690.

Non-Final Office Action issued Apr. 18, 2012 in U.S. Appl. No. 12/796,061, 7 pages.

Final Office Action issued Nov. 13, 2012 in U.S. Appl. No. 12/796,061, 18 pages.

Final Office Action issued Jun. 7, 2013 in U.S. Appl. No. 12/796,061, 21 pages.

Non-Final Office Action issued May 7, 2014 in U.S. Appl. No. 12/796,061, 29 pages.

Final Office Action issued Dec. 5, 2014 in U.S. Appl. No. 12/796,061, 31 pages.

Non-Final Office Action issued Oct. 8, 2015 in U.S. Appl. No. 12/796,061, 23 pages.

International Search Report and Written Opinion for Application No. PCT/US2010/037795, mailed Dec. 21, 2010, 11 pages.

Supplementary International Search Report for Application No. PCT/IB2010/001659, mailed Sep. 29, 2011, 3 pages.

\* cited by examiner

PHARMACEUTICAL DOSAGE FORM FOR ORAL ADMINISTRATION OF A BCL 2 FAMILY INHIBITOR

This application claims priority benefit of U.S. provisional application Ser. No. 61/185,130 filed on Jun. 8, 2009.

FIELD OF THE INVENTION

The present invention relates to a pharmaceutical dosage form for oral administration of Bcl-2 family inhibitors, a method of preparing the dosage form and a method of treating proliferative disorders.

BACKGROUND

Proteins of the Bcl-2 family, e.g. Bcl-2, Bcl-xL and Mcl-1, enable cells to evade apoptosis. These proteins are implicated in cancer and other proliferative diseases. They are often upregulated in cancer cells, where they sequester and neutralize proapoptotic proteins, thus enabling the survival of the cancer cells despite the presence of apoptosis-triggering signals. Consequently inhibitors of Bcl-2 family proteins are useful candidates for cancer therapy. Several inhibitors have been described, for example in WO 2007/040650.

A preferred Bcl-2 family inhibitor is N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), the preparation of which is described in US 2007/0027135. The molecular structure of ABT-263 is depicted below:

Unfortunately, the crystalline forms of these compounds are characterized by a more or less pronounced poor solubility in aqueous liquids which affects their dissolution rate and bioavailability. A measure of the potential usefulness of an oral dosage form of a pharmaceutical agent is the bioavailability observed after oral administration of the dosage form. Various factors can affect the bioavailability of a drug when administered orally. These factors include aqueous solubility, drug absorption throughout the gastrointestinal tract, dosage strength and first-pass effect. Aqueous solubility is one of the most important of these factors.

For a variety of reasons, such as patient compliance and taste masking, a solid dosage form is usually preferred over a liquid dosage form. In most instances, however, oral solid dosage forms of a drug provide a lower bioavailability than oral solutions of the drug.

There have been attempts to improve the bioavailability provided by solid dosage forms by forming solid solutions of drugs. Solid solutions are preferred physical systems because the components therein readily form liquid solutions when contacted with a liquid medium such as gastric juice. The ease of dissolution may be attributed at least in part to the fact that the energy required for dissolution of the components from a solid solution is less than that required for the dissolution of the components from a crystalline or microcrystalline solid phase. It is, however, important that the drug released from the solid solution remains water-solubilized in the aqueous fluids of the gastrointestinal tract; otherwise, the drug may precipitate in the gastrointestinal tract, resulting in low bioavailability.

WO 01/00175 discloses mechanically stable pharmaceutical dosage forms which are solid solutions of active ingredients in an auxiliary agent matrix. The matrix contains a homopolymer or a copolymer of N-vinyl pyrrolidone and a liquid or semi-solid surfactant.

WO 00/57854 discloses mechanically stable pharmaceutical dosage forms for peroral administration which contain at least one active compound, at least one thermo-plastically mouldable, matrix-forming auxiliary and more than 10% and up to 40% by weight of a surface-active substance that has an HLB of between 2 and 18, is liquid at 20° C., or has a drop point at between 20° C. and 50° C.

US 2005/0208082 discloses a solubilizing composition comprising a mixture of vitamin E TPGS and linoleic acid. The solubilizing composition is used to disperse a lipophile in an aqueous phase. The lipophile may be a therapeutically effective lipophile such as lipophilic vitamins, coenzyme Q10, carotenoids, alpha-lipoic acid or essential fatty acids.

US 2005/0236236 discloses pharmaceutical compositions for administration of hydrophobic drugs, particularly steroids. The pharmaceutical compositions include a hydrophobic drug, a vitamin E substance and a surfactant. The reference claims a synergistic effect between the hydrophobic drug and the vitamin E substance.

SUMMARY

Due to the presence of a sulfanyl group in its molecular structure, ABT-263 is prone to oxidation to sulfoxides which do not retain the therapeutic effect of ABT-263. For this reasons, oral liquid solutions of ABT-263 have been prepared immediately prior to use.

We now have found that a solid dispersion of ABT-263 and at least one pharmaceutically acceptable polymer not only shows adequate bioavailability after oral administration but also results in a storage-stable, ready-to-use dosage form. Quite surprisingly, in the solid dispersions the ABT-263 molecule, despite its essentially non-crystalline amorphous state, is largely resistant against oxidation even in presence of only a minor amount of antioxidant or the absence of an antioxidant. "Essentially non-crystalline amorphous state" means no more than 5%, preferably no more than 2% crystallinity, determined by X-ray diffraction analysis, and most preferably no detectable crystallinity, determined by polarization microscopy.

The invention relates to a pharmaceutical dosage form which comprises a solid dispersion product comprising a pharmaceutically active ingredient, at least one pharmaceutically acceptable polymer, and at least one pharmaceutically acceptable solubilizer, said pharmaceutically active ingredient being N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, a salt, hydrate or solvate thereof.

DETAILED DESCRIPTION

In the dosage forms of the invention, the active ingredient is present as a solid dispersion or as a solid solution. The term "solid dispersion" defines a system in a solid state (as opposed to a liquid or gaseous state) comprising at least two components, wherein one component is dispersed evenly throughout the other component or components. For example, the active ingredient or combination of active ingredients is dispersed in a matrix comprised of the pharmaceutically acceptable polymer(s) and pharmaceutically acceptable solubilizers. The term "solid dispersion" encompasses systems having small particles, typically of less than 1 μm in diameter, of one phase dispersed in another phase. When said dispersion of the components is such that the system is chemically and physically uniform or homogeneous throughout or consists of one phase (as defined in thermodynamics), such a solid dispersion will be called a "solid solution" or a "glassy solution". A glassy solution is a homogeneous, glassy system in which a solute is dissolved in a glassy solvent. Glassy solutions and solid solutions are preferred physical systems. These systems do not contain any significant amounts of active ingredients in their crystalline or microcrystalline state, as evidenced by thermal analysis (DSC) or X-ray diffraction analysis (WAXS).

The dosage forms according to the invention are characterized by an excellent stability and, in particular, exhibit high resistance against recrystallization or decomposition of the active ingredient(s).

The dosage forms of the present invention exhibit a release and absorption behaviour that is characterized by high attainable AUC (area under the plasma concentration-time curve from 0 to 48 hours or other indicated time intervals), high attainable $C_{max}$ (maximum plasma concentration), and low $T_{max}$ (time to reach maximum plasma concentration).

The term "AUC" means "Area Under the Curve" and is used in its normal meaning, i.e., as the area under the plasma concentration-time curve. "$AUC_{0-48}$" and "$AUC_{0-24}$" refer to the area under the plasma concentration-time curve from 0 to 48 hours or from 0 hours to 24 hours, respectively.

The dispersion formed upon contact with an aqueous liquid may also be useful as such, for example as oral liquid dosage form or parenteral injections.

Generally, the solid dispersion product comprises
from about 0.5 to 40% by weight, preferably from about 1 to 25% by weight, of ABT-263,
from about 40 to 97.5% by weight, preferably from about 50 to 94% by weight, of said at least one pharmaceutically acceptable polymer,
from about 2 to 20% by weight, preferably from about 5 to 20% by weight, of said at least one solubilizer, and
from about 0 to 15% by weight, preferably from about 0 to 10% by weight, of additives.

Whereas the dosage form of the invention may consist entirely of solid dispersion product, additives and adjuvants are usually used in formulating the solid dispersion product into the dosage forms. Generally, the dosage form comprises at least 10% by weight, preferably at least 40% by weight, and most preferred at least 45% by weight, of solid dispersion product, based on the total weight of the solid dosage form.

Typically, a single dosage form of the invention contains the equivalent of about 50 mg to about 1000 mg, preferably about 75 mg to about 600 mg, in particular about 100 mg to about 500 mg, of ABT-263.

The inventive dosage form comprises ABT-263 or a combination of ABT-263 with one or more other Bcl-2 family inhibitors. The dosage form may comprise a combination of ABT-263 and at least one further active ingredient.

ABT-263 may exist as acid addition salts, basic addition salts or zwitterions. Salts of ABT-263 are prepared during their isolation or following their purification. Acid addition salts are those derived from the reaction of ABT-263 with acid. Accordingly, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate and undecanoate salts of ABT-263 are meant to be embraced by this invention. Basic addition salts of compounds are those derived from the reaction of ABT-263 with the bicarbonate, carbonate, hydroxide or phosphate of cations such as lithium, sodium, potassium, calcium and magnesium.

In suitable embodiments, the pharmaceutically active ingredient is selected from the group consisting of the free base, the sodium salt and the dihydrochloride of ABT-263, or combinations thereof. In a preferred embodiment the pharmaceutically active ingredient is the free base of ABT-263.

The term "pharmaceutically acceptable solubilizer" as used herein refers to a pharmaceutically acceptable non-ionic surfactant. The solubilizer may effectuate an instantaneous emulsification of the active ingredient released from the dosage form and/or prevent precipitation of the active ingredient in the aqueous fluids of the gastrointestinal tract. A single solubilizer as well as combinations of solubilizers may be used. The solubilizer may be selected from the group consisting on non-ionic solubilizers, anionic solubilizers and combinations thereof. According to an embodiment of the invention, the solid dispersion product comprises a combination of two or more pharmaceutically acceptable solubilizers.

According to one embodiment of the invention the pharmaceutically acceptable non-ionic solubilizer is selected from the group consisting of polyol fatty acid esters, polyalkoxylated polyol fatty acid esters, polyalkoxylated fatty alcohol ethers, tocopheryl compounds or mixtures of two or more thereof, and the pharmaceutically acceptable anionic solubilizer is selected from the group consisting of alkyl sulfates, alkylcarboxylates, alkylbenzole sulfates and secondary alkane sulfonates.

Preferred non-ionic solubilizers are selected from sorbitan fatty acid esters, polyalkoxylated fatty acid esters such as, for example, polyalkoxylated glycerides, polyalkoxylated sorbitan fatty acid esters or fatty acid esters of polyalkylene glycols, polyalkoxylated ethers of fatty alcohols, tocopheryl compounds or mixtures of two or more thereof. A fatty acid chain in these compounds ordinarily comprises from 8 to 22 carbon atoms. The polyalkylene oxide blocks comprise on average from 4 to 50 alkylene oxide units, preferably ethylene oxide units, per molecule.

Suitable sorbitan fatty acid esters are sorbitan monolaurate, sorbitan monopalmitate, sorbitan monostearate (Span® 60), sorbitan monooleate (Span® 80), sorbitan tristearate, sorbitan trioleate, sorbitan monostearate, sorbitan monolaurate or sorbitan monooleate.

Examples of suitable polyalkoxylated sorbitan fatty acid esters are polyoxyethylene (20) sorbitan monolaurate, polyoxyethylene (20) sorbitan monopalmitate, polyoxyethylene (20) sorbitan monostearate, polyoxyethylene (20) sorbitan monooleate (Tween® 80), polyoxyethylene (20) sorbitan tristearate (Tween® 65), polyoxyethylene (20) sorbitan trioleate (Tween® 85), polyoxyethylene (4) sorbitan monostearate, polyoxyethylene (4) sorbitan monolaurate or polyoxyethylene (4) sorbitan monooleate.

Suitable polyalkoxylated glycerides are obtained for example by alkoxylation of natural or hydrogenated glycerides or by transesterification of natural or hydrogenated glycerides with polyalkylene glycols. Commercially available examples are polyoxyethylene glycerol ricinoleate 35, polyoxyethylene glycerol trihydroxystearate 40 (Cremophor® RH40, BASF AG) and polyalkoxylated glycerides like those obtainable under the proprietary names Gelucire® and Labrafil® from Gattefosse, e.g., Gelucire® 44/14 (lauroyl macrogol 32 glycerides prepared by transesterification of hydrogenated palm kernel oil with PEG 1500), Gelucire® 50/13 (stearoyl macrogol 32 glycerides, prepared by transesterification of hydrogenated palm oil with PEG 1500) or Labrafil M1944 CS (oleoyl macrogol 6 glycerides prepared by transesterification of apricot kernel oil with PEG 300).

A suitable fatty acid ester of polyalkylene glycols is, for example, PEG 660 hydroxystearic acid (polyglycol ester of 12-hydroxystearic acid (70 mol %) with 30 mol % ethylene glycol).

Suitable polyalkoxylated ethers of fatty alcohols are, for example, PEG (2) stearyl ether (Brij® 72), macrogol 6 cetylstearyl ether or macrogol 25 cetylstearyl ether.

In general, the tocopheryl compound corresponds to the formula below wherein Z is a linking group, $R^1$ and $R^2$ are, independently of one another, hydrogen or $C_1$-$C_4$ alkyl and n is an integer from 5 to 100, preferably 10 to 50. Typically, Z is the residue of an aliphatic dibasic acid such as glutaric, succinic, or adipic acid. Preferably, both $R^1$ and $R^2$ are hydrogen.

The preferred tocopheryl compound is alpha tocopheryl polyethylene glycol succinate, which is commonly abbreviated as vitamin E-TPGS. Vitamin E-TPGS is a water-soluble form of natural-source vitamin E prepared by esterifying d-alpha-tocopheryl acid succinate with polyethylene glycol 1000. Vitamin E-TPGS is available from Eastman Chemical Company, Kingsport, Tenn., USA, or from Cognis (Dusseldorf, Germany) and is listed in the US Pharmacopeia and National Formulary (NF).

According to one preferred embodiment of the invention the pharmaceutically acceptable solubilizer is selected from the group consisting of tocopheryl compounds having a polyalkylene glycol moiety (such as α-tocopheryl polyethylene glycol succinate), sorbitan fatty acid esters (such as sorbitan monolaurate) and polyoxyethylene sorbitan fatty acid esters (such as polyoxyethylene sorbitan monolaurate) and combinations of two or more thereof. This embodiment is particularly useful where the active ingredient is ABT-263 free base.

In another preferred embodiment the dosage form comprises at least one pharmaceutically acceptable non-ionic solubilizer and at least one pharmaceutically acceptable anionic solubilizer. Preferentially, the pharmaceutically acceptable non-ionic solubilizer is selected from the group consisting of sorbitan fatty acid esters, polyoxyethylene sorbitan fatty acid esters and α-tocopheryl polyethylene glycol succinate (also referred to herein as Vitamin E-TPGS or Vit. E-TPGS); and the pharmaceutically acceptable anionic solubilizer is sodium laurylsulfate (also referred to herein as SDS). This embodiment is particularly useful where the active ingredient is an acid addition salt of ABT-263 such as the dihydrochloride of ABT-263.

Formation of a ABT-263 solid solution can be promoted by incorporating a non-volatile solvent for the pharmaceutically active ingredient into the solid dispersion product. The non-volatile solvent is suitably selected from solvents with high dissolving power for ABT-263, which are liquid at ambient temperature and ambient pressure. Nonlimiting examples of suitable solvents comprise liquid polyethylene glycols, e.g., polyethylene glycol 400 (PEG-400); N-methylpyrrolidone; 1,3-bis(pyrrolidon-1-yl)-butane; and propylene glycol. A preferred solvent is propylene glycol. The amount of the non-volatile solvent to be used should not be so high as to compromise the mechanical properties of the solid dispersion product and usually is 2% to 10% by weight, based on the weight of the solid dispersion product, e.g., 3% to 5% by weight.

The pharmaceutically acceptable polymer may be selected from water-soluble polymers, water-dispersible polymers or water-swellable polymers or any mixture thereof. Polymers are considered water-soluble if they form a clear homogeneous solution in water. When dissolved at 20° C. in an aqueous solution at 2% (w/v), the water-soluble polymer preferably has an apparent viscosity of 1 to 5000 mPa·s, more preferably of 1 to 700 mPa·s, and most preferably of 5 to 100 mPa·s. Water-dispersible polymers are those that, when contacted with water, form colloidal dispersions rather than a clear solution. Upon contact with water or aqueous solutions, water-swellable polymers typically form a rubbery gel.

Preferably, the pharmaceutically acceptable polymer employed in the invention has a Tg of at least 40° C., preferably at least +50° C., most preferably from 80° C. to 180° C. "Tg" means glass transition temperature. Methods for determining Tg values of the organic polymers are described in "Introduction to Physical Polymer Science", 2nd Edition by L. H. Sperling, published by John Wiley & Sons, Inc., 1992. The Tg value can be calculated as the weighted sum of the Tg values for homopolymers derived from each of the individual monomers, i, that make up the polymer: $Tg = \Sigma W_i X_i$ where W is the weight percent of monomer i in the organic polymer, and X is the Tg value for the homopolymer derived from monomer i. Tg values for the homopolymers may be taken from "Polymer Handbook", 2nd Edition by J. Brandrup and E. H. Immergut, Editors, published by John Wiley & Sons, Inc., 1975.

Various additives contained in the solid dispersion product or even the active ingredient(s) itself may exert a plasticizing effect on the polymer and thus depress the Tg of the polymer such that the final solid dispersion product has a somewhat lower Tg than the starting polymer used for its preparation. In general, the final solid dispersion product has a Tg of 20° C. or higher, preferably 25° C. or higher, more preferably 30° C. or higher and most preferred 40° C. or higher, e.g., a Tg from about 45° C. to about 60° C.

For example, preferred pharmaceutically acceptable polymers can be selected from the group comprising homopolymers and copolymers of N-vinyl lactams, especially homopolymers and copolymers of N-vinyl pyrrolidone, e.g., polyvinylpyrrolidone (PVP), copolymers of N-vinyl pyrrolidone and vinyl acetate or vinyl propionate, cellulose esters and cellulose ethers, in particular methylcellulose and ethylcellulose, hydroxyalkylcelluloses, in particular hydroxypropylcellulose, hydroxyalkylalkylcelluloses, in particular hydroxypropylmethylcellulose, cellulose phthalates or succinates, in particular cellulose acetate phthalate and hydroxypropylmethylcellulose phthalate, hydroxypropylmethylcellulose succinate or hydroxypropylmethylcellulose acetate succinate; high molecular polyalkylene oxides such as polyethylene oxide and polypropylene oxide and copolymers of ethylene oxide and propylene oxide, polyvinyl alcohol-polyethylene glycol-graft copolymers (available as Kollicoat® IR from BASF AG, Ludwigshafen, Germany); polyacrylates and polymethacrylates such as methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), poly(hydroxyalkyl methacrylates), polyacrylamides, vinyl acetate polymers such as copolymers of vinyl acetate and crotonic acid, partially hydrolyzed polyvinyl acetate (also referred to as partially saponified "polyvinyl alcohol"), polyvinyl alcohol, oligo- and polysaccharides such as carrageenans, galactomannans and xanthan gum, or mixtures of one or more thereof.

Among these, homopolymers or copolymers of N-vinyl pyrrolidone, in particular a copolymer of N-vinyl pyrrolidone and vinyl acetate, are preferred. A particularly preferred polymer is a copolymer of 60% by weight of the copolymer, N-vinyl pyrrolidone and 40% by weight of the copolymer, vinyl acetate.

A further polymer which can be suitably used is Kollidon® SR (available from BASF AG, Ludwigshafen, Germany) which comprises a mixture of PVP and polyvinylacetate.

The solid dispersion product of the pharmaceutically active ingredient may be prepared by a variety of methods.

Preferably, the solid dispersion product is prepared by melt-extrusion. Accordingly, the solid dispersion product is a melt-processed, solidified mixture. The melt-extrusion process comprises the steps of preparing a homogeneous melt of the active ingredient or the combination of active ingredients, the pharmaceutically acceptable polymer and the solubilizers, and cooling the melt until it solidifies. "Melting" means a transition into a liquid or rubbery state in which it is possible for one component to become homogeneously embedded in the other. Typically, one component will melt and the other components will dissolve in the melt, thus forming a solution. Melting usually involves heating above the softening point of the pharmaceutically acceptable polymer. The preparation of the melt can take place in a variety of ways. The mixing of the components can take place before, during or after the formation of the melt. For example, the components can be mixed first and then melted or simultaneously mixed and melted. Usually, the melt is homogenized in order to disperse the active ingredients efficiently. Also, it may be convenient first to melt the pharmaceutically acceptable polymer and then to admix and homogenize the active ingredients.

Usually, the melt temperature is in the range of 70° C. to 250° C., preferably 80° C. to 180° C., most preferably 100° C. to 140° C.

The active ingredients can be employed as such or as a solution or dispersion in a suitable solvent such as alcohols, aliphatic hydrocarbons or esters. Another solvent which can be used is liquid carbon dioxide. The solvent is removed, e.g., evaporated, upon preparation of the melt. Alternatively, solid dispersions of the pharmaceutically active ingredient can also be prepared with a non-volatile solvent for the pharmaceutically active ingredient as previously mentioned.

Various additives may be included in the melt, for example flow regulators such as colloidal silica; lubricants, bulking agents (fillers), disintegrants, plasticizers, stabilizers such as antioxidants, light stabilizers, radical scavengers, or stabilizers against microbial attack.

The melting and/or mixing takes place in an apparatus customary for this purpose. Particularly suitable are extruders or kneaders. Suitable extruders include single screw extruders, intermeshing screw extruders or else multiscrew extruders, preferably twin screw extruders, which can be corotating or counterrotating and, optionally, equipped with kneading disks or other screw elements for mixing or dispersing the melt. It will be appreciated that the working temperatures will also be determined by the kind of extruder or the kind of configuration within the extruder used. Part of the energy needed to melt, mix and dissolve the components in the extruder can be provided by heating elements. However, the friction and shearing of the material in the extruder may also provide a substantial amount of energy to the mixture and aid in the formation of a homogeneous melt of the components.

The extrudate exiting from the extruder ranges from pasty to viscous. Before allowing the extrudate to solidify, the extrudate may be directly shaped into virtually any desired shape. Shaping of the extrudate may be conveniently carried out by a calender with two counter-rotating rollers with mutually matching depressions on their surface. A broad range of tablet forms can be attained by using rollers with different forms of depressions. If the rollers do not have depressions on their surface, films can be obtained. Alternatively, the extrudate is moulded into the desired shape by injection-moulding. Alternatively, the extrudate is subjected to profile extrusion and cut into pieces, either before (hot-cut) or after solidification (cold-cut).

Additionally, foams can be formed if the extrudate contains a propellant such as a gas, e.g., carbon dioxide, or a volatile compound, e.g., a low molecular-weight hydrocarbon, or a compound that is thermally decomposable to a gas. The propellant is dissolved in the extrudate under the relatively high pressure conditions within the extruder and, when the extrudate emerges from the extruder die, the pressure is suddenly released. Thus the solvability of the propellant is decreased and/or the propellant vaporises so that a foam is formed.

Optionally, the resulting solid solution product is milled or ground to granules. The granules may then be filled into capsules or may be compacted. Compacting means a process whereby a powder mass comprising the granules is densified under high pressure in order to obtain a compact with low porosity, e.g., a tablet. Compression of the powder mass is usually done in a tablet press, more specifically in a steel die between two moving punches.

Preferentially, the solid dosage form contains at least one additive selected from flow regulators, disintegrants, bulking agents and lubricants.

At least one additive selected from flow regulators, disintegrants, bulking agents (fillers) and lubricants is preferably used in compacting the granules. Disintegrants promote a rapid disintegration of the compact in the stomach and keep the liberated granules separate from one another. Suitable disintegrants are crosslinked polymers such as crosslinked polyvinyl pyrrolidone and crosslinked sodium carboxymethyl cellulose. Suitable bulking agents (also referred to as "fillers") are selected from mannitol, lactose, calcium hydrogen phosphate, microcrystalline cellulose (Avicel®), magnesium oxide, potato or corn starch, isomalt, polyvinyl alcohol.

Suitable flow regulators are selected from highly dispersed silica (Aerosil®) (also referred to herein as colloidal silicone dioxide), and animal or vegetable fats or waxes.

A lubricant is preferably used in compacting the granules. Suitable lubricants are selected from polyethylene glycol (e.g., having a molecular weight of from 1000 to 6000), magnesium and calcium stearates, sodium stearyl fumarate, talc, and the like.

Various other additives may be used, for example dyes such as azo dyes, organic or inorganic pigments such as aluminium oxide or titanium dioxide, or dyes of natural origin; stabilizers such as antioxidants, light stabilizers, radical scavengers, or stabilizers against microbial attack. Such additives are known to those skilled in the art, and non-limiting examples of, e.g., antioxidants comprise Vitamin E or derivatives thereof (e.g., Vitamin E-TPGS), butyl-hydroxytoluene (BTH), cysteine and ascorbic acid or derivatives thereof.

As previously mentioned the ABT-263 molecule is sensitive to thermal and/or oxidative degradation, giving rise to several degradation products, the exact structure of which has not been completely elucidated. It is believed that the major degradation products are sulfoxides formed by oxidation of the sulfanyl group of ABT-263. The tentative formula of the sulfoxide degradation product is shown below. It is apparent to the skilled person that the sulphur atom constitutes an asymmetry centre, giving rise to various diastereomeric forms, all of which should be included in the term "sulfoxide degradation products".

According to one embodiment, the dosage form comprises less than 1.5% by weight of sulfoxide decomposition products of the active ingredient, more preferably less than 1.2% and most preferably less than 0.9% by weight of sulfoxide decomposition products of the active ingredient, relative to the weight of the active ingredient.

Accordingly, a further aspect of the invention relates to a method of preparing a solid dosage form according to the invention, wherein a) a homogeneous melt of the pharmaceutically active ingredient, a salt, hydrate or solvate thereof, of the at least one pharmaceutically acceptable polymer and of the at least one solubilizer is prepared, and b) the melt is allowed to solidify to obtain a solid dispersion product.

According to a one embodiment, the method additionally comprises grinding said solid dispersion product and compressing said solid dispersion product into a tablet.

Dosage forms according to the invention may be provided as dosage forms consisting of several layers, for example laminated or multilayer tablets. They can be in open or closed form. "Closed dosage forms" are those in which one layer is completely surrounded by at least one other layer. Multilayer forms have the advantage that two active ingredients which are incompatible with one another can be processed, or that the release characteristics of the active ingredient(s) can be controlled. For example, it is possible to provide an initial dose by including an active ingredient in one of the outer layers, and a maintenance dose by including the active ingredient in the inner layer(s). Multilayer tablet types may be produced by compressing two or more layers of granules. Alternatively, multilayer dosage forms may be produced by a process known as "coextrusion". In essence, the process comprises the preparation of at least two different melt compositions as explained above, and passing these molten compositions into a joint coextrusion die. The shape of the coextrusion die depends on the required drug form. For example, dies with a plain die gap, called slot dies, and dies with an annular slit are suitable.

In order to facilitate the intake of such a dosage form by a mammal, it is advantageous to give the dosage form an appropriate shape. Large tablets that can be swallowed comfortably are therefore preferably elongated rather than round in shape.

A film coat on the tablet further contributes to the ease with which it can be swallowed. A film coat also improves taste and provides an elegant appearance. If desired, the film coat may be an enteric coat. The film coat usually includes a polymeric film-forming material such as hydroxypropyl-methylcellulose, hydroxypropylcellulose, and acrylate or methacrylate copolymers. Besides a film-forming polymer, the film coat may further comprise a plasticizer, e.g., polyethylene glycol, a surfactant, e.g., a Tween® type, and optionally a pigment, e.g., titanium dioxide or iron oxides. The film-coating may also comprise talc as anti-adhesive. The film coat usually accounts for less than about 5% by weight of the dosage form.

According to a further embodiment of the method of preparing a solid dosage form, the method additionally comprises grinding said solid dispersion product and filling said solid dispersion product into a capsule shell.

Suitable materials for capsule shells are known in the art, and comprise for example gelatin, gums such as carrageenan or gellan, and cellulose or cellulose derivatives such as hydroxypropylmethylcellulose.

According to one aspect of the invention the dosage form is used for treating a disease during which is overexpressed one or more of antiapoptotic Bcl-2 protein, antiapoptotic Bcl-$X_L$ protein and antiapoptotic Bcl-w protein.

According to another aspect of the invention the dosage form is used in a method for treating diseases of abnormal cell growth and/or dysregulated apoptosis, particularly proliferative disorders, comprising administering the dosage form to a subject in need thereof, and/or is used for manufacturing of a medicament for treating diseases of abnormal cell growth and/or dysregulated apoptosis, particularly proliferative disorders, wherein the treatment comprises administering the dosage form to a subject in need thereof.

Accordingly, the dosage forms of the invention are useful for treating proliferative disorders, especially tumors or cancers. The proliferative disorder may be selected from the group consisting of mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, cervical cancer, colon cancer, rectal cancer, cancer of the anal region, stomach cancer, gastrointestinal (gastric, colorectal and duodenal) cancer, chronic lymphocytic leukemia, acute lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and biliary duct), primary or secondary central nervous system tumor, primary or secondary brain tumor, Hodgkin's disease, chronic or acute leukemia, chronic myeloid leukemia, lymphocytic lymphoma, lymphoblastic leukemia, follicular lymphoma, lymphoid malignancies of T-cell or B-cell origin, melanoma, multiple myeloma, oral cancer, ovarian cancer, non-small-cell lung cancer, prostate cancer, small-cell lung cancer, cancer of the kidney and ureter, renal cell carcinoma, carcinoma of the renal pelvis, neoplasms of the central nervous system, primary central nervous system lymphoma, non-Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblastoma, and combinations thereof.

The exact dose and frequency of administration depends on the particular condition being treated, the age, weight and general physical condition of the particular patient as well as other medication the individual may be taking, as is well known to those skilled in the art.

The pharmaceutical dosage form of the present invention may be administered together with additional pharmaceutically active ingredients or comprise additional pharmaceutically active ingredients. Said additional pharmaceutically active ingredients may be compounds which are known to be useful for the treatment of proliferative disorders, either alone or in combination with other compounds.

Combination therapies illustratively include administration of a composition of the present invention concomitantly with one or more of bortezomib, carboplatin, cisplatin, cyclophosphamide, dacarbazine, dexamethasone, docetaxel, doxorubicin, etoposide, fludarabine, irinotecan, paclitaxel, rapamycin, rituximab, vincristine and the like, for example with a polytherapy such as CHOP (cyclophosphamide+doxorubicin+vincristine+prednisone), RCVP (rituximab+cyclophosphamide+vincristine+prednisone), R-CHOP (rituximab+CHOP) or DA-EPOCH-R (dose-adjusted etoposide, prednisone, vincristine, cyclophosphamide, doxorubicin and rituximab).

A composition of the invention can be administered in combination therapy with one or more therapeutic agents that include, but are not limited to, alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1 inhibitors), activators of a death receptor pathway, Bcr-Abl kinase inhibitors, BiTE (bi-specific T-cell engager) antibodies, antibody-drug conjugates, biological response modifiers, cyclin-dependent kinase (CDK) inhibitors, cell cycle inhibitors, cyclooxygenase-2 (COX-2) inhibitors, dual variable domain binding proteins (DVDs), human epidermal growth factor receptor 2 (ErbB2 or HER/2neu) receptor inhibitors, growth factor inhibitors, heat shock protein (HSP)-90 inhibitors, histone deacetylase (HDAC) inhibitors, hormonal therapies, immunologicals, inhibitors of apoptosis proteins (IAPB), intercalating antibiotics, kinase inhibitors, kinesin inhibitors, JAK2 inhibitors, mammalian target of rapamycin (mTOR) inhibitors, microRNAs, mitogen-activated extracellular signal-regulated kinase (MEK) inhibitors, multivalent binding proteins, non-steroidal anti-inflammatory drugs (NSAIDs), poly-ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteasome inhibitors, purine analogs, pyrimidine analogs, receptor tyrosine kinase inhibitors, retinoids, deltoids, plant alkaloids, small inhibitory ribonucleic acids (siRNAs), topoisomerase inhibitors, ubiquitin ligase inhibitors, and the like.

BiTE antibodies are bi-specific antibodies that direct T-cells to attack cancer cells by simultaneously binding the two cells. The T-cell then attacks the target cancer cell. Examples of BiTE antibodies include, but are not limited to, adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (Sutton et al. (1997) *J. Immunol.* 158:5783-5790).

siRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263 or ABT-737 in various tumor cell lines (Tse et al. (2008) *Cancer Res.* 68:3421-3428 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy-chain DVD polypeptides and two light-chain DVD polypeptides are referred to as DVD Ig's. Each half of a DVD Ig comprises a heavy-chain DVD polypeptide, a light-chain DVD polypeptide, and two antigen binding sites. Each binding site comprises a heavy-chain variable domain and a light-chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, Cloretazine™ (laromustine, VNP 40101M), cyclophosphamide, dacarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, treosulfan, trofosfamide and the like.

Angiogenesis inhibitors include epidermal growth factor receptor (EGFR) inhibitors, endothelial-specific receptor tyrosine kinase (Tie-2) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include Alimta™ (pemetrexed disodium, LY231514, MTA), 5-azacitidine, Xeloda™ (capecitabine), carmofur, Leustat™ (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethenylcytidine, fludarabine, 5-fluorouracil (5-FU) alone or in combination with leucovorin, Gemzar™ (gemcitabine), hydroxyurea, Alkeran™ (melphalan), mercaptopurine, 6-mercaptopurine riboside, methotrexate, mycophenolic acid, nelarabine, nolatrexed, ocfosfate, pelitrexol, pentostatin, raltitrexed, ribavirin, S-1, triapine, trimetrexate, TS-1, tiazofurin, tegafur, vidarabine, UFT and the like.

Antivirals include ritonavir, hydroxychloroquine and the like.

Aurora kinase inhibitors include ABT-348, AZD-1152, MLN-8054, VX-680, aurora A-specific kinase inhibitors, aurora B-specific kinase inhibitors, pan-aurora kinase inhibitors and the like.

Bcl-2 family protein inhibitors other than ABT-263 include AT-101 ((−)gossypol), Genasense™ Bcl-2-targeting antisense oligonucleotide (G3139 or oblimersen), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), GX-070 (obatoclax) and the like.

Bcr-Abl kinase inhibitors include dasatinib (BMS-354825), Gleevec™ (imatinib) and the like.

CDK inhibitors include AZD-5438, BMI-1040, BMS-387032, CVT-2584, flavopyridol, GPC-286199, MCS-5A, PD0332991, PHA-690509, seliciclib (CYC-202 or R-roscovitine), ZK-304709 and the like.

COX-2 inhibitors include ABT-963, Arcoxia™ (etoricoxib), Bextra™ (valdecoxib), BMS-347070, Celebrex™ (celecoxib), COX-189 (lumiracoxib), CT-3, Deramaxx™ (deracoxib), JTE-522, 4-methyl-2-(3,4-dimethylphenyl)-1-(4-sulfamoylphenyl)-1H-pyrrole, MK-663 (etoricoxib), NS-398, parecoxib, RS-57067, SC-58125, SD-8381, SVT-2016, S-2474, T-614, Vioxx™ (rofecoxib) and the like.

EGFR inhibitors include ABX-EGF, anti-EGFR immunoliposomes, EGF-vaccine, EMD-7200, Erbitux™ (cetuximab), HR3, IgA antibodies, Iressa™ (gefitinib), Tarceva™ (erlotinib or OSI-774), TP-38, EGFR fusion protein, Tykerb™ (lapatinib) and the like.

ErbB2 receptor inhibitors include CP-724714, CI-1033 (canertinib), Herceptin™ (trastuzumab), Tykerb™ (lapatinib), Omnitarg™ (2C4, petuzumab), TAK-165, GW-572016 (ionafamib), GW-282974, EKB-569, PI-166, dHER2 (HER2 vaccine), APC-8024 (HER2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17AAG, CNF-101, CNF-1010, CNF-2024, 17-DMAG, geldanamycin, IPI-504, KOS-953, Mycograb™ (human recombinant antibody to HSP-90), nab-17AAG, NCS-683664, PU24FCl, PU-3, radicicol, SNX-2112, STA-9090, VER-49009 and the like.

Inhibitors of apoptosis proteins include HGS-1029, GDC-0145, GDC-0152, LCL-161, LBW-242 and the like.

Antibody-drug conjugates include anti-CD22-MC-MMAF, anti-CD22-MC-MMAE, anti-CD22-MCC-DM1, CR-011-vcMMAE, PSMA-ADC, MEDI-547, SGN-19A, SGN-35, SGN-75 and the like.

Activators of death receptor pathway include TRAIL and antibodies or other agents that target TRAIL or death receptors (e.g., DR4 and DR5) such as apomab, conatumumab, ETR2-ST01, GDC0145 (lexatumumab), HGS-1029, LBY-135, PRO-1762, trastuzumab and the like.

Kinesin inhibitors include Eg5 inhibitors such as AZD-4877 and ARRY-520, CENPE inhibitors such as GSK-923295A, and the like.

JAK2 inhibitors include CEP-701 (lesaurtinib), XL019, NCB-018424 and the like.

MEK inhibitors include ARRY-142886, ARRY-438162, PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30 and Torin 1, and the like.

Non-steroidal anti-inflammatory drugs include Amigesic™ (salsalate), Dolobid™ (diflunisal), Motrin™ (ibuprofen), Orudis™ (ketoprofen), Relafen™ (nabumetone), Feldene™ (piroxicam), ibuprofen cream, Aleve™ and Naprosyn™ (naproxen), Voltaren™ (diclofenac), Indocin™ (indomethacin), Clinoril™ (sulindac), Tolectin™ (tolmetin), Lodine™ (etodolac), Toradol™ (ketorolac), Daypro™ (oxaprozin) and the like.

PDGFR inhibitors include CP-673451, CP-868596 and the like.

Platinum chemotherapeutics include cisplatin, Eloxatin™ (oxaliplatin), eptaplatin, lobaplatin, nedaplatin, Paraplatin™ (carboplatin), picoplatin, satraplatin and the like.

Polo-like kinase inhibitors include BI-2536 and the like.

Phosphoinositide-3 kinase inhibitors include wortmannin, LY-294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include Avastin™ (bevacizumab), ABT-869, AEE-788, Angiozyme™ (a ribozyme that inhibits angiogenesis (Ribozyme Pharmaceuticals (Boulder, Colo.) and Chiron (Emeryville, Calif.)), axitinib (AG-13736), AZD-2171, CP-547632, IM-862, Macugen™ (pegaptanib), Nexavar™ (sorafenib, BAY43-9006), pazopanib (GW-786034), vatalanib (PTK-787 or ZK-222584), Sutent™ (sunitinib or SU-11248), VEGF trap, Zactima™ (vandetanib or ZD-6474) and the like.

Antibiotics include intercalating antibiotics such as aclarubicin, actinomycin D, amrubicin, annamycin, Adriamycin™ (doxorubicin), Blenoxane™ (bleomycin), daunorubicin, Caelyx™ and Myocet™ (liposomal doxorubicin), elsamitrucin, epirubicin, glarubicin, idarubicin, mitomycin C, nemorubicin, neocarzinostatin, peplomycin, pirarubicin, rebeccamycin, stimalamer, streptozocin, Valstar™ (valrubicin), zinostatin and the like.

Topoisomerase inhibitors include aclarubicin, 9-aminocamptothecin, amonafide, amsacrine, becatecarin, belotecan, BN-80915, Camptosar™ (irinotecan hydrochloride), camptothecin, Cardioxane™ (dexrazoxane), diflomotecan, edotecarin, Ellence™ and Pharmorubicin™ (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include Avastin™ (bevacizumab), CD40-specific antibodies, chTNT-1/B, denosumab, Erbitux™ (cetuximab), Humax-CD4™ (zanolimumab), IGF1R-specific antibodies, lintuzumab, Panorex™ (edrecolomab), Rencarex™ (WX G250), Rituxan™ (rituximab), ticilimumab, trastuzumab, CD20 antibodies types I and II and the like.

Hormonal therapies include Arimidex™ (anastrozole), Aromasin™ (exemestane), arzoxifene, Casodex™ (bicalutamide), Cetrotide™ (cetrorelix), degarelix, deslorelin, Desopan™ (trilostane), dexamethasone, Drogenil™ (flutamide), Evista™ (raloxifene), Afema™ (fadrozole), Fareston™ (toremifene), Faslodex™ (fulvestrant), Femara™ (letrozole), formestane, glucocorticoids, Hectorol™ (doxercalciferol), Renagel™ (sevelamer carbonate), lasofoxifene, leuprolide acetate, Megace™ (megestrol), Mifeprex™ (mifepristone), Nilandron™ (nilutamide), tamoxifen including Nolvadex™ (tamoxifen citrate), Plenaxis™ (abarelix), prednisone, Propecia™ (finasteride), rilostane, Suprefact™ (buserelin), luteinizing hormone releasing hormone (LHRH) including Trelstar™ (triptorelin), histrelin including Vantas™ (histrelin implant), Modrastane™ (trilostane), Zoladex™ (goserelin) and the like.

Deltoids and retinoids include seocalcitol (EB1089 or CB1093), lexacalcitol (KH1060), fenretinide, Panretin™ (alitretinoin), tretinoin including Atragen™ (liposomal tretinoin), Targretin™ (bexarotene), LGD-1550 and the like.

PARP inhibitors include ABT-888, olaparib, KU-59436, AZD-2281, AG-014699, BSI-201, BGP-15, INO-1001, ONO-2231 and the like.

Plant alkaloids include vincristine, vinblastine, vindesine, vinorelbine and the like.

Proteasome inhibitors include Velcade™ (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, Actimmune™ (interferon gamma-1b), interferon gamma-n1, combinations thereof and the like. Other agents include Alfaferone (IFN-α), BAM-002 (oxidized glutathione), Beromun™ (tasonermin), Bexxar™ (tositumomab), Campath™ (alemtuzumab), CTLA4 (cytotoxic lymphocyte antigen 4), dacarbazine, denileukin, epratuzumab, Granocyte™ (lenograstim), lentinan, leukocyte alpha interferon, imiquimod, MDX-010 (anti-CTLA-4), melanoma vaccine, mitumomab, molgramostim, Mylotarg™ (gemtuzumab ozogamicin), Neupogen™ (filgrastim), OncoVAC-CL, Ovarex™ (oregovomab), pemtumomab (Y-muHMFG1), Provenge™ (sipuleucel-T), sargaramostim, sizofuran, teceleukin, Theracys™ (BCG or Bacillus Calmette-Guerin), ubenimex, Virulizin™ (immunotherapeutic, Lorus Pharmaceuticals), Z-100 (Specific Substance of Maruyama or SSM), WF-10 (tetrachlorodecaoxide or TCDO), Proleukin™ (aldesleukin), Zadaxin™ (thymalfasin), Zenapax™ (daclizumab), Zevalin™ (90Y-ibritumomab tiuxetan) and the like.

Biological response modifiers are agents that modify defense mechanisms of living organisms or biological responses, such as survival, growth or differentiation of tissue cells to direct them to have anti-tumor activity, and include krestin, lentinan, sizofuran, picibanil, PF-3512676 (CpG-8954), ubenimex and the like.

Pyrimidine analogs include cytarabine (cytosine arabinoside, ara C or arabinoside C), doxifluridine, Fludara™ (fludarabine), 5-FU (5-fluorouracil), floxuridine, Gemzar™

(gemcitabine), Tomudex™ (raltitrexed), triacetyluridine, Troxatyl™ (troxacitabine) and the like.

Purine analogs include Lanvis™ (thioguanine), Purinethol™ (mercaptopurine) and the like.

Antimitotic agents include batabulin, epothilone D (KOS-862), N-(2-((4-hydroxy-phenyl)amino)pyridin-3-yl)-4-methoxybenzenesulfonamide, ixabepilone (BMS-247550), paclitaxel, Taxotere™ (docetaxel), larotaxel (PNU-100940, RPR-109881 or XRP-9881), patupilone, vinflunine, ZK-EPO (synthetic epothilone) and the like.

Ubiquitin ligase inhibitors include MDM2 inhibitors such as nutlins, NEDD8 inhibitors such as MLN4924, and the like.

Compositions of this invention can also be used as radiosensitizers that enhance the efficacy of radiotherapy. Examples of radiotherapy include, but are not limited to, external beam radiotherapy (XBRT), teletherapy, brachytherapy, sealed-source radiotherapy, unsealed-source radiotherapy and the like.

Additionally or alternatively, a composition of the present invention can be administered in combination therapy with one or more antitumor or chemotherapeutic agents selected from Abraxane™ (ABI-007), ABT-100 (farnesyl transferase inhibitor), Advexin™ (Ad5CMV-p53 vaccine or contusugene ladenovec), Altocor™ or Mevacor™ (lovastatin), Ampligen™ (poly(I)-poly(C12U), a synthetic RNA), Aptosyn™ (exisulind), Aredia™ (pamidronic acid), arglabin, L-asparaginase, atamestane (1-methyl-3,17-dione-androsta-1,4-diene), Avage™ (tazarotene), AVE-8062 (combretastatin derivative), BEC2 (mitumomab), cachectin or cachexin (tumor necrosis factor), Canvaxin™ (melanoma vaccine), Cea-Vac™ (cancer vaccine), Celeuk™ (celmoleukin), histamine including Ceplene™ (histamine dihydrochloride), Cervarix™ (AS04 adjuvant-adsorbed human papilloma virus (HPV) vaccine), CHOP (Cytoxan™ (cyclophosphamide)+Adriamycin™ (doxorubicin)+Oncovin™ (vincristine)+prednisone), combretastatin A4P, Cypat™ (cyproterone), DAB(389)EGF (catalytic and translocation domains of diphtheria toxin fused via a His-Ala linker to human epidermal growth factor), dacarbazine, dactinomycin, Dimericine™ (T4N5 liposome lotion), 5,6-dimethylxanthenone-4-acetic acid (DMXAA), discodermolide, DX-8951f (exatecan mesylate), eniluracil (ethynyluracil), squalamine including Evizon™ (squalamine lactate), enzastaurin, EPO-906 (epothilone B), Gardasil™ (quadrivalent human papilloma virus (Types 6, 11, 16, 18) recombinant vaccine), Gastrimmune™, Genasense™ (oblimersen), GMK (ganglioside conjugate vaccine), GVAX™ (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, Junovan™ and Mepact™ (mifamurtide), lonafarnib, 5,10-methylenetetrahydrofolate, miltefosine (hexadecylphosphocholine), Neovastat™ (AE-941), Neutrexin™ (trimetrexate glucuronate), Nipent™ (pentostatin), Onconase™ (ranpirnase, a ribonuclease enzyme), Oncophage™ (vitespen, melanoma vaccine treatment), OncoVAX™ (IL-2 vaccine), Orathecin™ (rubitecan), Osidem™ (antibody-based cell drug), Ovarex™ MAb (murine monoclonal antibody), paclitaxel albumin-stabilized nanoparticle, paclitaxel, Pandimex™ (aglycone saponins from ginseng comprising 20(S)-protopanaxadiol (aPPD) and 20(S)-protopanaxatriol (aPPT)), panitumumab, Panvac™-VF (investigational cancer vaccine), pegaspargase, peginterferon alfa (PEG interferon A), phenoxodiol, procarbazine, rebimastat, Removab™ (catumaxomab), Revlimid™ (lenalidomide), RSR13 (efaproxiral), Somatuline™ LA (lanreotide), Soriatane™ (acitretin), staurosporine (Streptomyces staurospores), talabostat (PT100), Targretin™ (bexarotene), Taxoprexin™ (docosahexaenoic acid (DHA)+paclitaxel), Telcyta™ (canfosfamide, TLK-286), Temodar™ (temozolomide), tesmilifene, tetrandrine, thalidomide, Theratope™ (STn-KLH vaccine), Thymitaq™ (nolatrexed dihydrochloride), TNFerade™ (adenovector: DNA carrier containing the gene for tumor necrosis factor-α), Tracleer™ or Zavesca™ (bosentan), TransMID-107R™ (KSB-311, diphtheria toxins), tretinoin (retin-A), Trisenox™ (arsenic trioxide), Ukrain™ (derivative of alkaloids from the greater celandine plant), Virulizin™, Vitaxin™ (anti-αvβ3 antibody), Xcytrin™ (motexafin gadolinium), Xinlay™ (atrasentan), Xyotax™ (paclitaxel poliglumex), Yondelis™ (trabectedin), ZD-6126 (N-acetylcolchinol-O-phosphate), Zinecard™ (dexrazoxane), zoledronic acid, zorubicin and the like.

EXAMPLES

The following examples will serve to further illustrate the invention without limiting it.

Example 1

Preparation and Characterization of Solid Dispersion Products

Formulations of various compositions were produced as shown in Table 1 below. ABT-263 was mixed in a blender with a pre-granulated mixture of Copovidone (copolymer of N-vinyl pyrrolidone and vinyl acetate) and the solubilizer(s). Where indicated, 1% of colloidal silicon dioxide was added to improve flow properties. The powdery mixture was extruded in a Leistritz micro 18 GMP-extruder at an extrusion temperature as shown in Table 1.

Absolute bioavailability compares the bioavailability (estimated as the area under the curve, or AUC) of the active drug in systemic circulation following oral administration with the bioavailability of the same drug following intravenous administration. In Table 1 the bioavailability F was determined after administering an ABT-263 dose of 50 mg to fed dogs.

TABLE 1

|  | Formulation | | | | | | | |
| --- | --- | --- | --- | --- | --- | --- | --- | --- |
|  | 1 | 2 | 3 | 4 | 5 | 6 | 7 | 8 |
| ABT-263 | 10% 2HCl | 10.7% 2HCl | 10.7% 2HCl | 10.7% 2HCl | 10% 2HCl | 10% 2HCl | 10% 2HCl | 10% 2HCl |
| Copovidone (%) | 80 | 72.3 | 72.3 | 72.3 | 80 | 79 | 80 | 79 |
| PS-20 (%) | 10 | 10 |  | 5 |  |  |  |  |
| Span 20 (%) |  |  |  |  | 5 | 5 |  |  |
| Vitamin E-TPGS (%) |  | 10 | 2 |  |  |  | 5 | 5 |

TABLE 1-continued

| | | | | | | | | |
|---|---|---|---|---|---|---|---|---|
| SDS (%) | | 6 | 6 | 6 | | | | |
| PG (%) | | | | 3 | 5 | 5 | 5 | 5 |
| Coll. Silicone Dioxide (%) | | 1 | 1 | 1 | | 1 | | 1 |
| Extrusion Temp. (° C.) | 140 | 140 | 140 | 140 | 140 | 140 | 130 | 130 |
| Sum of degradation products (%) | 1.83 | 1.11 | 1.22 | 1.05 | 2.78 | 1.07 | 1.68 | 0.93 |
| Sum of sulfoxides (%) | N/D | 0.77 | 0.71 | 0.69 | N/D | N/D | N/D | N/D |
| F (%) | 27.5 | 32.6 | 25.9 | 27.0 | 31.7 | N/D | 26.7 | N/D |
| F (%) for comparative lipid solution in same study* | 22.4 | 31.5 | 29.2 | 29.2 | 22.4 | N/D | 22.4 | N/D |
| relative F (%)** | 122.8 | 103.5 | 88.7 | 92.5 | 141.5 | | 119.2 | |

| | Formulation | | | | | | |
|---|---|---|---|---|---|---|---|
| | 9 | 10 | 11 | 12 | 13 | 14 | 15 |
| ABT-263 | 10.7% 2HCl | 10.7% 2HCl | 10.7% 2HCl | 10% Na | 10% f.b. | 10% f.b. | 10.7% 2HCl |
| Copovidone (%) | 78.3 | 78.3 | 72.3 | 79 | 79 | 79 | 72.3 |
| PS-20 (%) | | | | 10 | | | |
| Span 20 (%) | | | | | | | 10 |
| Vitamin E-TPGS (%) | 5 | 5 | 5 | | 10 | 10 | |
| SDS (%) | | | 5 | | | | 6 |
| PG (%) | 5 | 5 | 5 | | | | |
| Coll. Silicone Dioxide (%) | 1 | 1 | 1 | 1 | 1 | 1 | 1 |
| Extrusion Temp. (° C.) | 130 | 135 | 140 | 130 | 125 | 130 | 130 |
| Sum of degradation products (%) | 0.66 | 0.83 | 1.23 | 0.73 | 0.80 | 0.41 | 1.27 |
| Sum of sulfoxides (%) | 0.37 | 0.42 | 0.72 | 0.29 | 0.43 | 0.30 | 0.62 |
| F (%) | N/D | 29.6 | N/D | 32.1 | 33.7 | N/D | N/D |
| F (%) for comparative lipid solution in same study* | N/D | N/D | N/D | 31.5 | N/D | N/D | N/D |
| relative F (%)** | | | | 101.9 | | | |

Abbreviations used:
"2HCl", dihydrochloride salt of ABT-263;
"Na", sodium salt of ABT-263;
"f.b.", free base of ABT-263;
"PS-2", Polysorbate 20;
"SDS", sodium lauryl sulfate;
"Vitamin E-TPGS", alpha tocopheryl polyethylene glycol succinate;
"PG", propylene glycol;
N/D, not determined
*25 mg ABT-263/ml in Phosal 53 NCC/ethanol (90:10)
**calculated by taking the bioavailability F for the comparative lipid solution as 100%

Example 2

Bioavailability Evaluation a) Protocol for the Oral Bioavailability Studies

For bioavailability evaluation, extrudates as described in Example 1 were milled and filled into capsules. Each capsule contained 50 mg ABT-263.

The dose response and food effect for two formulations were evaluated in beagle dogs (both genders, approximate weight: 10 kg). Groups of 5 dogs each received a 50 mg (1 capsule/dog), 100 mg (2 capsules/dog) or 200 mg (4 capsules/dog) mg oral dose of ABT-263 under both fasting and fed conditions. The dose was followed by approximately 10 milliliters of water. For all studies, beagle dogs were fasted overnight prior to dosing, but were permitted water ad libitum. Food was returned to the dogs ~30 minutes prior to dosing (fed conditions) or 4 hours after dosing (fasting conditions). A washout/recovery period of one week separated the two dosing periods. Blood samples were obtained from each animal prior to dosing and at convenient time points chosen among 0.25, 0.5, 1.0, 1.5, 2, 3, 4, 6, 9, 12, 15, 24, 36 and 48 hours after drug administration. The plasma was separated from the red cells by centrifugation and frozen (−30° C.) until analysis. Concentrations of ABT-263 were determined by reverse phase HPLC-MS/MS following liquid-liquid extraction of the plasma samples. The area under the curve (AUC) was calculated by the trapezoidal method over the time course of the study. Each dosage form was evaluated in a group containing 5 dogs; the values reported are averages for each group of dogs.

b) Influence of Dosage and Application to Fasted or Fed Dogs

Figure 1:
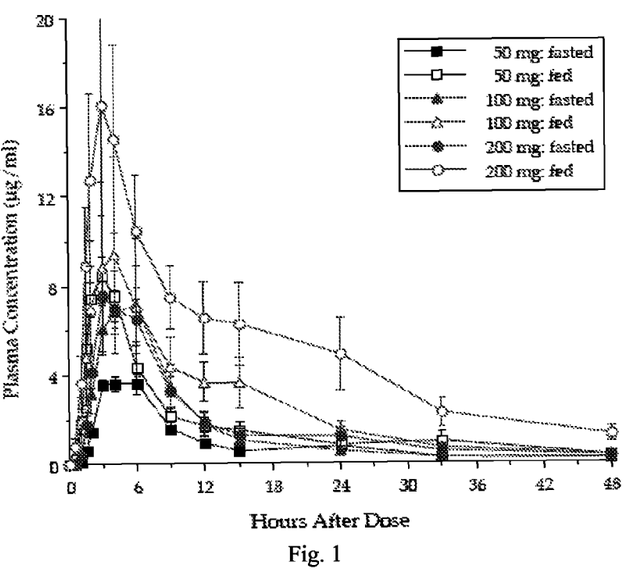
FIG. 1 shows at different time points the plasma concentration of ABT-263 administered as dihydrochloride salt in a formulation containing Span 20 as solubilizer, wherein the formulation orally has been administered in doses of 50, 100 or 200 mg to fasted or fed dogs.
Figure 2:
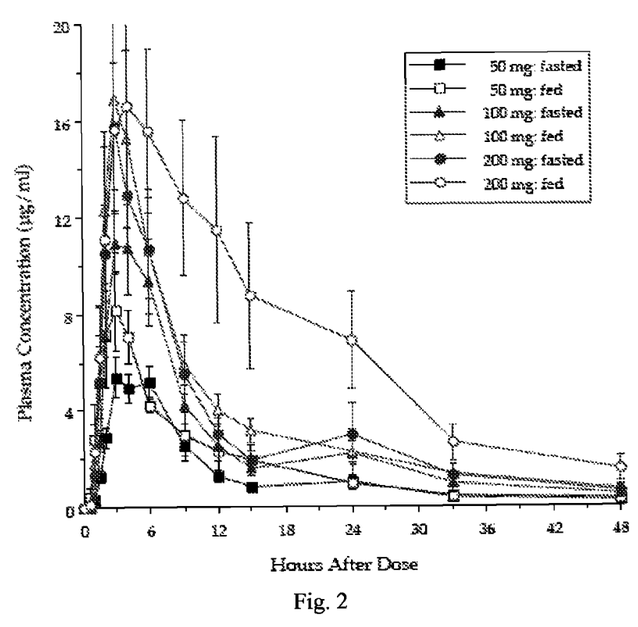
FIG. 2 shows at different time points the plasma concentration of ABT-263 administered as dihydrochloride salt in a formulation containing Vitamin E-TPGS as solubilizer, wherein the formulation orally has been administered in doses of 50, 100 or 200 mg to fasted or fed dogs.

Formulations 6 or 8 of ABT 263 as defined in Table 1 were administered to fasted or fed dogs in dosages corresponding to the amounts of ABT-263 as indicated in FIG. 1 and FIG. 2. Subsequently, the plasma concentrations of ABT-263 were determined from blood samples taken at the indicated time points. In FIG. 1 and FIG. 2 open and closed symbols represent fed or fasted dogs, respectively. Squares, triangles and circles represent a dose of 50 mg, 100 mg, or 200 mg ABT-263, respectively.

For both formulations plasma concentrations of ABT-263 were higher when administered to fed dogs. This effect was more prominent at higher dosages of 100 mg and 200 mg. In fed dogs a dose linearity could be observed. AUC values of Formulation 6 in fasted dogs were 40-60% lower than in fed dogs. When Formulation 8 was administered AUC values were approximately 30% lower in fasted dogs.

c) Comparison of a Free Base Formulation vs. an HCl-Salt Formulation

Fed dogs received orally one of the following two formulations as one capsule containing Formulation 13 or Formulation 10 as indicated in Table 1, equivalent to an amount of 50 mg ABT-263.

Figure 3:
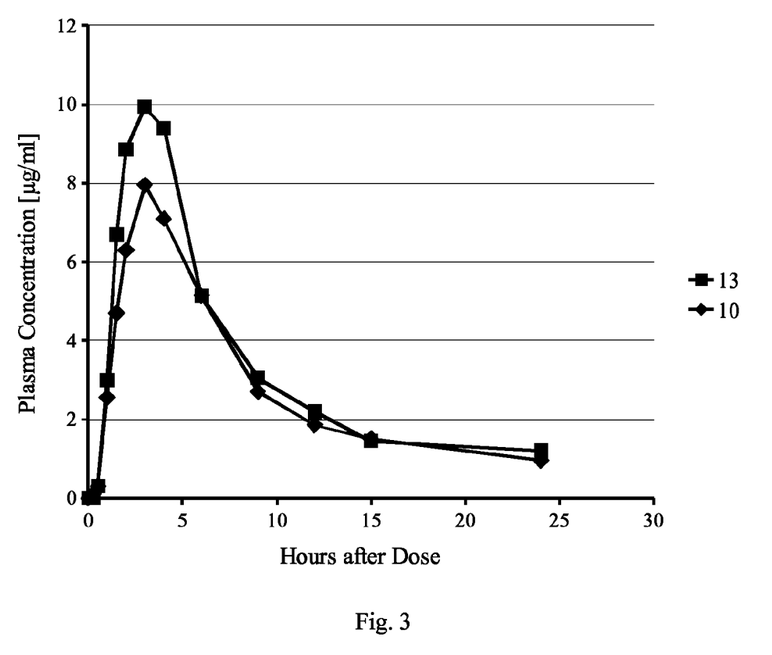
FIG. 3 shows at different time points the plasma concentration of ABT-263 administered as free base in a formulation containing Vitamin E-TPGS only (Formulation 13), or as dihydrochloride salt in a formulation containing Vitamin E-TPGS plus propylene glycol as plasticizer (Formulation 10), wherein the formulation orally has been administered at a dose of 50 mg to fed dogs.

The plasma concentrations of ABT-263 were determined from blood samples taken at the time points as indicated in FIG. 3, which shows the mean plasma concentration of five dogs treated with Formulation 13 or Formulation 10, respectively.

The bioavailability data obtained from this experiment are summarized in Table 2 below (shown as mean value of 6 animals; standard deviation in brackets).

TABLE 2

| Formulation | $C_{max}$ | $C_{max}/D$ | $T_{max}$ | AUC | AUC/D | F |
|---|---|---|---|---|---|---|
| 13 | 10.4 (2.1) | 2.03 | 3.2 (0.5) | 78.7 (15.7) | 15.3 | 33.7 (5.5) |
| 10 | 8.6 (0.7) | 1.74 | 3.6 (0.6) | 67.6 (7.9) | 13.4 | 29.6 (3.4) |

$C_{max}$: maximum concentration of ABT-263 in plasma (unit: μg/ml)
$C_{max}/D$: maximum concentration per dose (unit: μg/ml per mg/kg)
$T_{max}$: time to maximum plasma concentration (unit: h)
AUC: area under the plasma concentration curve (unit: μg·hr/ml)
AUC/D: area under curve per dose (unit: μg·hr/ml per mg/kg)
F: average bioavailability (unit: %)

Example 3

Storage Stability

For selected formulations (6 and 8 according to Table 1) the storage stability was determined. The formulations were kept in closed containers at ambient conditions (approximately 19° C. to 25° C. at RH of 60% or less). The ABT-263 content and the content of degradation products of the active ingredient including sulfoxides was determined at the beginning of the storage period (initial value) and after 4 months by separation via HPLC (or UPLC) and detection with a UV/VIS detector. The results are shown in Table 3 below.

TABLE 3

|  | Formulation | |
|---|---|---|
|  | 6 | 8 |
| Content (initial) | 97.8% | 97.0% |
| degradation products (initial) | 1.07% | 0.93% |
| Content (after 4 months) | 96.7% | 98.9% |
| degradation products (after 4 months) | 1.16% | 0.96% |

The formulations were chemically stable as content and impurity levels remained unchanged upon storage.

Example 4

Determination of Sulfoxide Formation

The formulations 2, 3, 12, 4, 9, 11, 10, 13 and 14 as defined in Table 1 were assessed for sulfoxide formation in an accelerated stability study, using exposure in an open dish at a relative humidity of 40° C./75%. The sulfoxide content was determined at the beginning of the experiment (less than 0.8% in all cases), after 1 week, 3 weeks and 6 weeks for the formulations referred to in FIG. 4, and at time points chosen among 4 weeks, 5 weeks and 7 weeks for the formulations referred to in FIG. 5.

Figure 4:
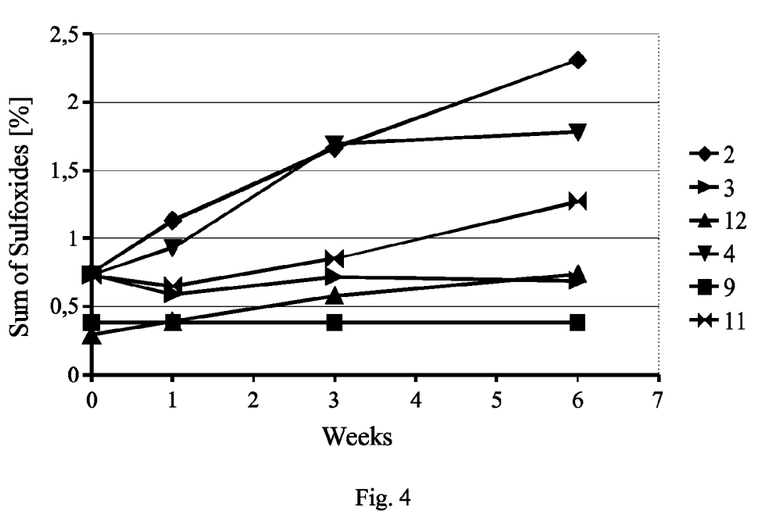
FIG. 4 and FIG. 5 show the results of an accelerated stability study using open dishes, wherein the sulfoxide content of different ABT-263 formulations was determined a different time points.
Figure 5:
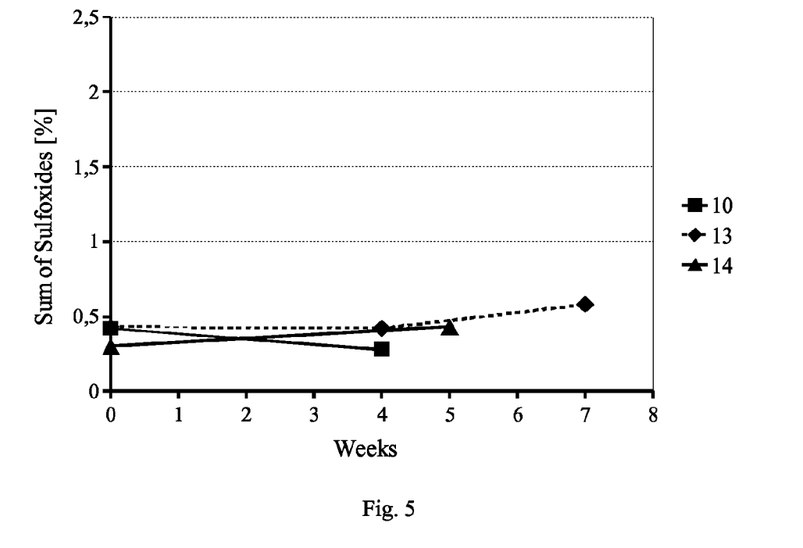

The data shown in FIG. 4 indicate that lower extrusion temperatures cause lower contents of sulfoxides. Comparatively low levels of sulfoxides were also observed in the formulations referred to in FIG. 5, all of which were extruded at temperatures of 135° C. or less. Sulfoxide contents increased most significantly with formulations 2 and 4, both of which contain polysorbate 20. Therefore, the inclusion of polysorbate 20 appears to promote the formation of sulfoxides.

Figure 6:
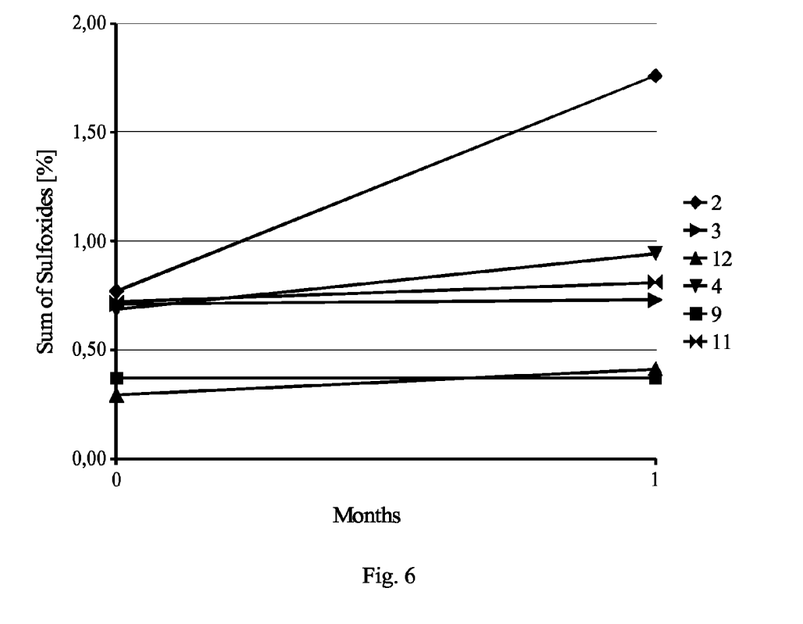
FIG. 6 and FIG. 7 show the results of an accelerated stability study using closed bottles, wherein the sulfoxide content of different ABT-263 formulations was determined at different time points.
Figure 7:
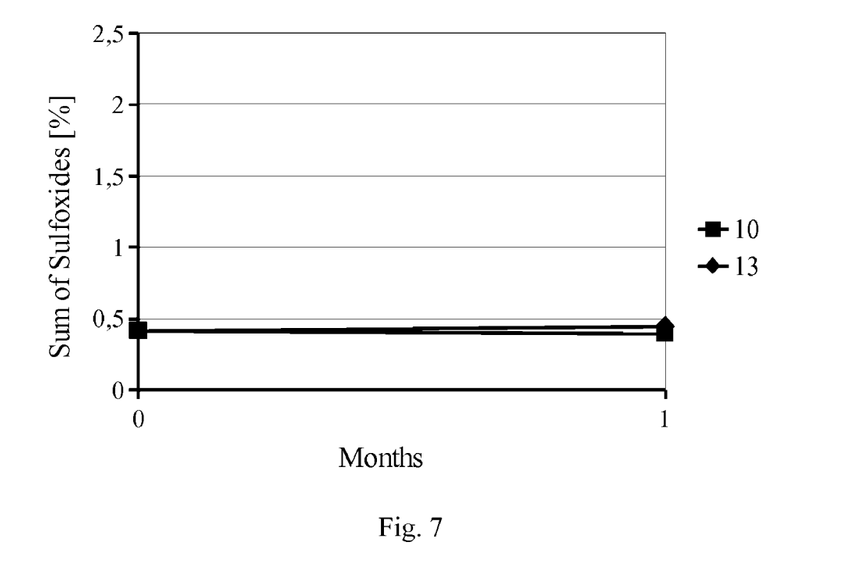

In a second experiment sulfoxide formation was determined in samples, which were kept in closed 1.5 oz HDPE bottles at a relative humidity of 40° C./75 percent. The results are shown in FIG. 6 and FIG. 7.

Example 5

Crystallinity of ABT-263 Extrudates

The formulations 9, 2, 13 and 14 as defined in Table 1 were manufactured, using the process parameters as indicated in Table 4 below. The extrudates were evaluated for the presence of crystalline active ingredient by polarisation microscopy.

TABLE 4

| | Formulation | | | |
|---|---|---|---|---|
| | 10 | 13 | 14 | 15 |
| | Process parameters: | | | |
| Feed rate | 0.5 kg/h | 1.0 kg/h | 1.0 kg/h | 0.5 kg/h |
| Temperature | 135° C. | 125° C. | 130° C. | 130° C. |
| | Process data: | | | |
| Crystallinity | detected | not detected | not detected | not detected |

Example 6

Crystallinity of ABT-263 Extrudates Upon Prolonged Storage

Various extrudates as indicated in Table 5 were kept at accelerated aging conditions in open dishes or closed bottles. At the indicated time points the presence of crystalline active ingredient was evaluated by polarisation microscopy.

TABLE 5

| | Physical stability (crystallinity) | | | | |
|---|---|---|---|---|---|
| | Time | | | | |
| | 0 weeks | 1 week | 3 weeks | 6 weeks | 1 month |
| Storage conditions | open dish 40° C./75% RH | | | | 1.5 oz HDPE bottles, closed, 40° C./75% RH |
| 2 | detected (++) | detected (++) | detected (++) | detected (++) | detected (++) |

TABLE 5-continued

Physical stability (crystallinity)

| | Time | | | | |
|---|---|---|---|---|---|
| | 0 weeks | 1 week | 3 weeks | 6 weeks | 1 month |
| 3 | detected (++) | detected (++) | detected (++) | detected (++) | detected (++) |
| 12 | not detected | not detected | not detected | not detected | not detected |
| 4 | not detected | detected (+) | detected (++) | detected (++) | detected (++) |
| 9 | detected (+) | not detected | not detected | detected (+) | detected (+) |
| 11 | detected (+) | detected (++) | detected (++) | detected (++) | detected (++) |
| 10 | detected (+) | detected (+) | detected (+) | detected (+) | detected (+) |
| 13 | not detected | not detected | not detected | not detected | not detected |
| 14 | not detected | not detected | not detected | not detected | not detected |

(+) few crystals detected
(++) numerous crystals detected

Example 7

Manufacture of Tablets

Following the procedure of Example 1, an extrudate was obtained from the solid dispersion product ingredients listed in Table 6 below. Extrudates from Example 1 was milled and the powder was blended with the tableting excipients listed in Table 6. A single punch tablet press was used to prepare tablets containing 50 mg of ABT-263.

TABLE 6

Tablet composition

| | Formulation | | |
|---|---|---|---|
| | 16 | 17 | 18 |
| Extrudate (ABT-263 free base:Copovidone:Vitamin E-TPGS:Coll.Silicone Dioxide 10:79:10:1) | 98% | 83% | 83% |
| Croscarmellose Sodium | | | 15% |
| Mannitol | | 15% | |
| Coll. Silicone Dioxide | 1.0% | 1.0% | 1.0% |
| Sodium stearyl fumarate | 1.0% | 1.0% | 1.0% |
| Total tablet mass | 510.2 mg | 602.4 mg | 602.4 mg |

Figure 8:
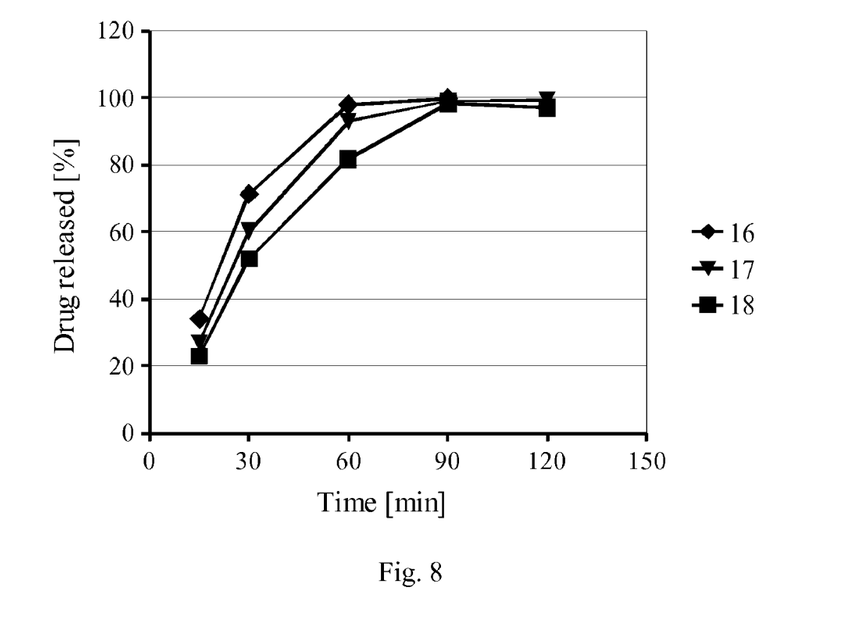
FIG. 8 shows the release of ABT-263 from tablets containing different ABT-263 formulations.

The tablets were immersed in 0.1N HCl at a temperature of 37° C. (to mimic stomach conditions) and stirred by paddle rotation at a speed of 75 rounds per minute (rpm). The amount of released ABT-263 was determined at various time points by HPLC-UV/VIS. The results are shown in FIG. 8.

What is claimed is:

1. A pharmaceutical dosage form comprising:
   N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, a salt, a hydrate, or a solvate thereof;
   at least one pharmaceutically acceptable polymer comprising a copolymer of N-vinyl pyrrolidone; and,
   a single pharmaceutically acceptable solubilizer, said single pharmaceutically acceptable solubilizer being a tocopheryl compound having a polyalkylene glycol moiety;
   wherein the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, the salt, the hydrate, or the solvate thereof is dispersed within a solid dispersion product in a concentration from 0.5 to 40% by weight, the solid dispersion product further comprising from 40 to 97.5% by weight of the at least one pharmaceutically acceptable polymer and from 2 to 20% by weight of the single pharmaceutically acceptable solubilizer.

2. The dosage form of claim 1, wherein the tocopheryl compound having a polyalkylene glycol moiety is an alpha tocopheryl polyethylene glycol succinate.

3. The dosage form of claim 1, wherein the solid dispersion further comprises a non-volatile solvent for the pharmaceutically active ingredient, said solvent being a liquid at ambient temperature and ambient pressure.

4. The dosage form of claim 3, wherein said non-volatile solvent is propylene glycol.

5. The dosage form of claim 1, wherein said pharmaceutically active ingredient is selected from the group consisting of the free base, the sodium salt and the dihydrochloride salt of N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, and combinations thereof.

6. The dosage form of claim 1, containing at least one additive selected from flow regulators, disintegrants, bulking agents and lubricants.

7. The dosage form of claim 1, wherein the solid dispersion product comprises additives, wherein the concentration of the additives is less than 15% by weight of the solid dispersion product.

8. The dosage form of claim 1, wherein the solid dispersion comprises sulfoxide decomposition products, and further wherein the concentration of sulfoxide decomposition products is less than 1.5% by weight relative to the weight of the active ingredient.

9. The dosage form of claim 1, wherein the solid dispersion comprises sulfoxide decomposition products, and further wherein the concentration of sulfoxide decomposition products is less than 1.2% by weight relative to the weight of the active ingredient.

10. The dosage form of claim 1, wherein the solid dispersion comprises sulfoxide decomposition products, and further wherein the concentration of sulfoxide decomposition products is less than 0.9% by weight relative to the weight of the active ingredient.

11. The dosage form of claim 1, wherein the solid dispersion product is a melt-processed, solidified mixture.

12. A method for treating a proliferative disorder, comprising administering the dosage form of claim 1 to a subject in need thereof.

13. The method of claim 12, wherein the proliferative disorder is selected from tumors and cancers.

14. The method of claim 13, wherein the proliferative disorder is selected from the group consisting of mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, cervical cancer, colon cancer, rectal cancer, cancer of the anal region, stomach cancer, gastrointestinal (gastric, colorectal and duodenal) cancer, chronic lymphocytic leukemia, acute lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and biliary duct), primary or secondary central nervous system tumor, primary or secondary brain tumor, Hodgkin's disease, chronic or acute leukemia, chronic myeloid leukemia, lymphocytic lymphoma, lymphoblastic leukemia, follicular lymphoma, lymphoid malignancies of T-cell or B-cell origin, melanoma, multiple myeloma, oral cancer, ovarian cancer, non-small-cell lung cancer, prostate cancer, small-cell lung cancer, cancer of the kidney and ureter, renal cell carcinoma, carcinoma of the renal pelvis, neoplasms of the central nervous system, primary central nervous system lymphoma, non-Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblastoma, and combinations thereof.

15. A process for preparing a solid dosage form of claim 1, comprising: (a) preparing a homogeneous melt of the pharmaceutically active ingredient or a salt, hydrate or solvate thereof, the at least one pharmaceutically acceptable polymer and the single solubilizer, and (b) allowing the melt to solidify to obtain a solid dispersion product.

16. The process of claim 15, further comprising grinding said solid dispersion product and compressing said solid dispersion product into a tablet.

17. The process of claim 15, further comprising grinding said solid dispersion product and filling said solid dispersion product into a capsule shell.

18. The dosage form of claim 1, wherein said pharmaceutically active ingredient comprises the free base of N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

19. The dosage form of claim 1, wherein said pharmaceutically active ingredient comprises non-crystalline, amorphous N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

20. A solid dispersion product consisting of:
from 0.5 to 40% by weight of a pharmaceutically active ingredient being N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, a salt, hydrate or solvate thereof;
from 40 to 97.5% by weight of at least one pharmaceutically acceptable polymer being a copolymer of N-vinyl pyrrolidone;
from 2 to 20% by weight of a single pharmaceutically acceptable solubilizer being a tocopheryl compound having a polyalkylene glycol moiety;
from 2% to 10% by weight of a non-volatile solvent for the pharmaceutically active ingredient, said solvent being a liquid at ambient temperature and ambient pressure; and
colloidal silicon dioxide.

21. A pharmaceutical dosage form consisting of:
a solid dispersion product consisting of from 0.5 to 40% by weight of a pharmaceutically active ingredient being N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, a salt, hydrate or solvate thereof; from 40 to 97.5% by weight of at least one pharmaceutically acceptable polymer being a copolymer of N-vinyl pyrrolidone; from 2 to 20% by weight of a single pharmaceutically acceptable solubilizer being a tocopheryl compound having a polyalkylene glycol moiety; from 2% to 10% by weight of a non-volatile solvent for the pharmaceutically active ingredient, said solvent being a liquid at ambient temperature and ambient pressure; and colloidal silicon dioxide;
a disintegrant;
a bulking agent;
a flow regulator; and
a lubricant.

22. The dosage form of claim 6, containing the flow regulator, wherein the flow regulator comprises colloidal silicon dioxide.

* * * * *

UNITED STATES PATENT AND TRADEMARK OFFICE
CERTIFICATE OF CORRECTION

Page 1 of 1

PATENT NO. : 9,642,796 B2
APPLICATION NO. : 12/796000
DATED : May 9, 2017
INVENTOR(S) : Claudia Packhaeuser et al.

It is certified that error appears in the above-identified patent and that said Letters Patent is hereby corrected as shown below:

On the Title Page

In Assignee, delete "AbbVie Inc., North Chicago, IL (US)" and insert therefor -- AbbVie Deutschland GmbH & Co KG, Wiesbaden (DE) --.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*